United States Patent
Chen (10) Patent No.: US 6,196,058 B1
(45) Date of Patent: Mar. 6, 2001

(54) ON-LINE VISCOSITY MEASUREMENT SYSTEM

(75) Inventor: Qingyuan Chen, Atlanta, GA (US)

(73) Assignee: Consolidated Papers, Inc., Wisconsin Rapids, WI (US)

( * ) Notice: Subject to any disclaimer, the term of this patent is extended or adjusted under 35 U.S.C. 154(b) by 0 days.

(21) Appl. No.: 09/041,180

(22) Filed: Mar. 12, 1998

(51) Int. Cl.$^7$ .................................. G01N 11/04
(52) U.S. Cl. ........................................ 73/54.04
(58) Field of Search ............... 73/54.09, 54.06, 73/54.04, 54.07, 54.01

(56) References Cited

U.S. PATENT DOCUMENTS

| | | |
|---|---|---|
| 3,677,069 | 7/1972 | Rubin et al. . |
| 3,838,598 | * 10/1974 | Tompkins ................ 73/861.52 |
| 3,924,448 | 12/1975 | Howard et al. ................ 73/55 |
| 4,118,973 | 10/1978 | Tucker et al. . |
| 4,165,632 | 8/1979 | Weber et al. ................ 73/55 |
| 4,573,345 | 3/1986 | Krutchen et al. ............ 73/56 |
| 4,680,957 | * 7/1987 | Dodd ........................ 73/54.07 |
| 4,726,219 | * 2/1988 | Pearson et al. ............ 73/54.04 |
| 4,750,351 | * 6/1988 | Ball ............................ 73/54.04 |
| 4,817,416 | 4/1989 | Blanch et al. . |
| 4,821,564 | * 4/1989 | Pearson et al. ............ 73/152.31 |
| 4,992,487 | * 2/1991 | Rao ............................... 523/303 |
| 5,172,585 | * 12/1992 | Gleissle ...................... 73/54.04 |
| 5,272,912 | 12/1993 | Katsuzaki . |
| 5,359,881 | 11/1994 | Kalotay et al. . |
| 5,597,949 | 1/1997 | Kalotay ......................... 73/54 |
| 5,637,790 | 6/1997 | de Corral ....................... 73/54 |
| 5,877,409 | 3/1999 | Girling .......................... 73/54 |

FOREIGN PATENT DOCUMENTS

| | | |
|---|---|---|
| 595276 | 5/1994 | (EP) . |
| 2162954A | 2/1986 | (GB) . |
| WO96 01988 | 1/1996 | (WO) . |

OTHER PUBLICATIONS

Hughes et al, Schaum's Outline of Theory and Problems of Fluid Dynamics, 1967, pp. 235–236, McGraw Hill.*

"On Line Viscosity Measurement with Coriolis Mass Flow Meters," Instrument Society of America, 1991, ISA/91, Advances in Instrumentation and Control, P. Kalotay and D. Schaffer, vol. 46, Part 2, pp. 1029–1039.

"Viscosity Measurement with Micro Motion Mass Flowmeters," Micro Motion, Inc., 1994, pp. 1–17.

* cited by examiner

Primary Examiner—Hezron Williams
Assistant Examiner—Jay L Politzer
(74) Attorney, Agent, or Firm—Greer, Burns & Crain, Ltd.

(57) ABSTRACT

An improved method and apparatus for determining fluid viscosity comprises conveying substantially fully developed, uni-directional, and undisturbed fluid flow through a differential pressure measurement section and flow rate measuring means connected in line with, but separated from, the differential pressure measurement section. A preceding flow tube section is connected to the inlet of the differential pressure measurement section, and a succeeding flow tube section is connected to the outlet of the differential pressure measurement section so that entrance and exit flow effects are avoided in the measurement section. Differential pressure measured in substantially undisturbed, uni-directional, and fully developed fluid flow results in improved accuracy of viscosity calculation using the Hagen-Poiseuille equation.

10 Claims, 3 Drawing Sheets

ON-LINE VISCOSITY MEASUREMENT SYSTEM

BACKGROUND OF THE INVENTION

The present invention relates to an improved method and apparatus for measuring the viscosity of fluids while flowing on-line in an industrial process.

Viscometers of many different configurations are presently used to measure the viscosity of fluids. Common among these viscometers are capillary type devices. In capillary viscometers fluid is usually accelerated by an external pressure to flow from a reservoir through a capillary and then to exit to air. For Newtonian fluids, the well known Navier-Stokes equations can be used to directly derive the Hagen-Poiseuille equation to determine viscosity:

$$\mu = (\pi \Delta p R^4)/(8 \Delta L Q)$$

where R is pipe diameter, Q is volumetric flow rate, $\Delta p$ is pressure differential, and $\Delta L$ is a length over which pressure differential is measured. This equation derives fluid viscosity from the pressure drop that occurs within a fluid body as it flows through a cylindrical tube. Application of the Hagen-Poiseuille equation, however, is limited to laminar flows (Reynolds numbers of less than 2100), and assumes steady, fully developed, undisturbed and unidirectional flow through a level tube of uniform diameter. One must also consider whether the fluid is Newtonian or non-Newtonian.

In terms of rheological behavior, fluids may be classified as Newtonian or non-Newtonian. Newtonian fluids have a viscosity which is constant regardless of the shear rate applied to the fluid, whereas for non-Newtonian fluids viscosity may vary as shear stress changes.

An acceptable model in which to describe shear sensitive behavior of non-Newtonian fluids is to treat them as "power law" fluids, whose viscosity within a specified operating range is approximated by a power law equation:

$$\mu = k \dot{y}^{n-1}$$

where $\mu$ is fluid viscosity, $\dot{y}$ is a shear rate and k and n are power law constants. For these fluids, the shear rate dependent viscosity at the pipe wall can be solved for using (for purposes of this application this equation will be referred to as "Equation A"):

$$\mu = K(\Delta P/Q)(4n/(3n+1)) \qquad \text{(Equation A)}$$

where n is the power law index, and $K = (\pi R^4/8 \Delta L)$ is a constant. This equation, as with the Hagen-Poiseuille equation for Newtonian fluids, assumes steady, fully developed, undisturbed and unidirectional flow through a level tube of uniform diameter.

Prior art capillary viscometers measure fluid flow rate and the pressure drop occurring as the fluid flows a known distance. Because of the configuration of these prior art capillary viscometer configurations, however, the fluid undergoes contraction when it enters the measurement tube and expansion when it exits the measurement tube ("entrance and exit effects"). Also, other flow disturbances can occur through the measuring section of these prior configurations. These factors may result in fluid flow which may be unsteady, not fully developed, and may not be unidirectional through the measuring section. Thus the underlying assumptions of the Hagen-Poiseuille equation and Equation A may be violated.

In order to accurately apply these equations to these prior art capillary viscometers, a $\Delta L$ equal to the distance that steady, unidirectional, and fully developed flow occurs would need to be known. This $\Delta L$ may not actually be equal to the nominal measured length of the capillary measurement section (a constant), but will instead be an unknown shorter length within the capillary over which steady, fully developed flow occurs. This $\Delta L$ will depend on the flow rate, making it a flow dependent variable, and is difficult to determine. The $\Delta p$ used in the Hagen Poiseuille equation and Equation A will also of course vary with differing $\Delta L$'s, further complicating accurate application of the equations to prior art capillary viscometers.

These problems in the past have been addressed by introducing complicated correction formulae to approximate for entrance and exit effects, so that the $\Delta L$ nominal length of the viscometer measurement section may be used. These formulae can be difficult and time consuming to apply, may introduce uncertainty to viscosity determination, and are flow rate dependent, requiring that they be evaluated and reapplied for each given flow rate.

Many industrial processes require an accurate measurement of a process fluid's viscosity. In the paper making and coating industry, for instance, the viscosity of a coating suspension will affect the ability to effectively apply the coating suspension to a base sheet, as well as affecting the weight and quality of the resultant dried coating layer. The viscosity of the fluid in this example is therefore a required process parameter. In this example, as in many others, the viscosity of the fluid will be somewhat dynamic, changing with time and operation conditions, such as flow rate. It is therefore desirable to achieve a continuous reading of the fluid viscosity, preferably while it is "on line" in the process stream.

Because of its scale, the general capillary viscometer configuration does not lend itself well to these industrial applications that require an on-line viscosity measurement in processes which generally use standard pipe sizes of a much larger than capillary scale. For these industrial on-line viscometer applications, a process flow is typically diverted through a section of piping configured specifically to measure viscosity. The configuration is typically similar to that of the above described capillary viscometer, except that it is in a larger scale. The flow may be diverted and regulated by use of a pump or other means, and a measuring section of piping is often configured with a flow meter and pressure measuring instrumentation.

In addition to some of the problems discussed above associated with a capillary viscometer configuration, this larger scale on-line configuration may introduce various additional problems to application of either the Hagen-Poiseuille equation or Equation A. Because the fluid diversion is inherently intrusive to the flow, the diverted flow is often disturbed. Also, the pumping of the fluid, as well as the presence of a flow meter, may further introduce flow disturbances and unsteadiness. Some devices used to measure flow rate, e.g., gear pumps, may also have leakage, leading to error in flow rate measurements.

Others have attempted to address some of these problems. Specifically, it is known to place a Coriolis mass flow meter, equipped with a differential pressure transducer, directly in the process flowpath. The differential pressure transducer measures the pressure drop between a point upstream of the meter and a point downstream of the meter, the distance between points being a known constant. This configuration has the advantage of the flow remaining in the process line. But, because of the looped configuration of a Coriolis meter, this viscometer configuration introduces flow disturbances, leading to violations of the assumptions underlying the equations. Also, this improved configuration does not address the entrance and exit effects that occur as flow enters and exits the measurement section. These disturbances and effects lead to fluid flow in the measurement section that is not fully developed and uni-directional. This results in further inaccuracies in the application of Equation A and the Hagen-Poiseuille equation. The effective ΔL to be used in these equations will not be equal to the distance between pressure measuring points, but will instead need to be experimentally determined for different fluids and flow rates.

There is therefor an unresolved need in industry for an on-line viscometer which features a flow path that avoids entrance and exit effects, and that provides for undisturbed, fully developed, and unidirectional fluid flow. Such a viscometer will allow for more accurate application of the Hagen-Poiseuille expression and Equation A.

OBJECTS OF THE INVENTION

It is an object of the present invention to provide an apparatus and method useful for industrial on-line applications with an improved flow path configuration for a more accurate application of either the Hagen-Poiseuille equation or Equation A in determining fluid viscosity.

SUMMARY OF THE INVENTION

The present invention comprises an improved apparatus for and method of measuring the viscosity of a flowing fluid.

The apparatus of the invention comprises a differential pressure measurement and a separate flow rate measurement section. The differential pressure measurement section comprises a differential pressure measurement flow tube connected to preceding and succeeding flow tubes. These preceding and succeeding flow tubes are configured such that flow entrance and exit effects are avoided, and such that fully developed, undisturbed, and unidirectional flow occurs through the pressure measurement flow tube. These flow conditions satisfy the assumptions underlying the Hagen-Poiseuille equation and Equation A, and therefore lead to accurate application of the equations to calculate fluid viscosity.

The differential pressure measurement section is substantially straight, and is of uniform inside diameter. In the preferred embodiment of the invention, the differential pressure measurement section is leveled. The differential pressure of the fluid between the pressure measurement flow tube inlet and outlet is measured using non-intrusive means to prevent flow disturbances. A preferred embodiment of the apparatus comprises a Rosemount model 3051C Coplanar Smart Pressure Transmitter along with WIKA Type 981.10 chemical seals (for non-invasive pressure taps) for this purpose. The length of the pressure measurement flow tube is such that differential pressure measurements of a meaningful magnitude may be obtained between its inlet and outlet.

A preceding straight flow tube with a diameter substantially equal to that of the measurement flow tube is connected to the inlet of the measurement tube. Likewise, a succeeding straight flow tube, also with a diameter substantially equal to that of the measurement tube, is connected to the outlet of the pressure measurement flow tube. The inside diameter of the preceding and succeeding flow tubes are substantially equal to that of the measurement flow tube so as to prevent fluid contraction and expansion effects as fluid enters and exits the measurement section. To further prevent any flow disturbances, the preceding and succeeding tubes are connected to the measurement flow tube with non-invasive connecting means to result in a smooth inner diameter pipe wall transition from measuring section to preceding and succeeding tube sections.

The length of the preceding and succeeding tubes are such that entrance and exit effects in the measurement section will be eliminated, and fluid flow will be fully developed, undisturbed, and unidirectional through the measurement flow tube. The length of the preceding tube should be at least as long as calculated by the formula L=0.035D×Re, where D is the inside tube diameter, and Re is the Reynolds number. The length of the succeeding flow tube should be at least 15 times the tube diameter. In one embodiment of the invention, the flow tubes have an inside diameter of about 1.61 inches, the preceding tube length is about 72 inches (accommodating Reynolds numbers of up to 1200), and the succeeding flow tube length is approximately 40 inches.

Because fluid flow in the measurement section does not experience entrance or exit effects, is fully developed, unidirectional, and undisturbed, the apparatus of the invention allows for accurate application of the Hagen-Poiseuille equation and Equation A to determine viscosity. All of the assumptions underlying these expressions are satisfied, and no correction formulae need be applied.

The flow rate measurement section of the invention measures the fluid flow rate, and comprises a non-intrusive flow meter or other flow measuring device connected in line with and located either upstream or downstream of the pressure measurement section. By measuring the flow rate at a point in line with, but removed from the pressure measurement section, accurate flow rate values can be measured without introducing any flow disturbances to the differential pressure measurement section. In the preferred embodiment of the apparatus, a Micro Motion ELITE CMF 200 Coriolis mass flow meter, with fluid density measuring capability, placed downstream of the succeeding flow tube is used to measure fluid flow rate. The preferred embodiment further comprises a Micro Motion ELITE RFT9739 Mass Flow and Density Transmitter in conjunction with the ELITE mass flow meter to transmit output mass flow and density signals.

In the preferred embodiment of the invention, fluid temperature is also measured in line with the pressure measurement section flue tubes in a non-intrusive manner with a resistance temperature detector probe placed downstream of the mass flow meter. This preferred embodiment of the apparatus adjusts measured pressure differential, measured density, and measured flow rate for temperature expansion and contraction effects. Also, although temperature is not used directly to calculate viscosity, temperature data are useful as fluid viscosities can vary greatly with temperature.

Fluid flow is generated using a pump or other similar means. The flow should be generated in a manner such that fluctuations are kept to a minimum. In the preferred embodiment of the apparatus, a Moyno positive displacement pump with capacity of 0–60 gpm is used.

The preferred embodiment of the apparatus also comprises a microcomputer to receive, convert, calculate, dynamically display, and record values including the fluid viscosity, mass flow rate, fluid density, differential pressure, temperature, Reynolds number and velocity. The microcomputer is programmed to calculate apparent viscosity using the Hagen-Poiseuille equation. In this preferred embodiment, the microcomputer also performs averaging over many signal readings to reduce flow fluctuation error.

A method for determining the viscosity versus shear rate relationship for non-Newtonian fluids comprises measuring differential pressures under several different shear rates (flow rates), and then using these results to derive power law constants. In the preferred embodiment, the microcomputer is programmed to perform this function. A log-log plot of differential pressure verses shear rate (flow rate) will be approximately linear with a slope equal to the power law index n. The y axis intercept will be equal to a constant from which the power law consistency k may be derived. The preferred embodiment of the invention utilizes the well known least squares fit method to solve for a best linear fit for the given data.

As fluid viscosity is often referenced in the paper and coating industry in Brookfield units, in the preferred embodiment of the invention, the microcomputer is also programmed to extrapolate Brookfield viscosity.

DETAILED DESCRIPTION

Figure 1:
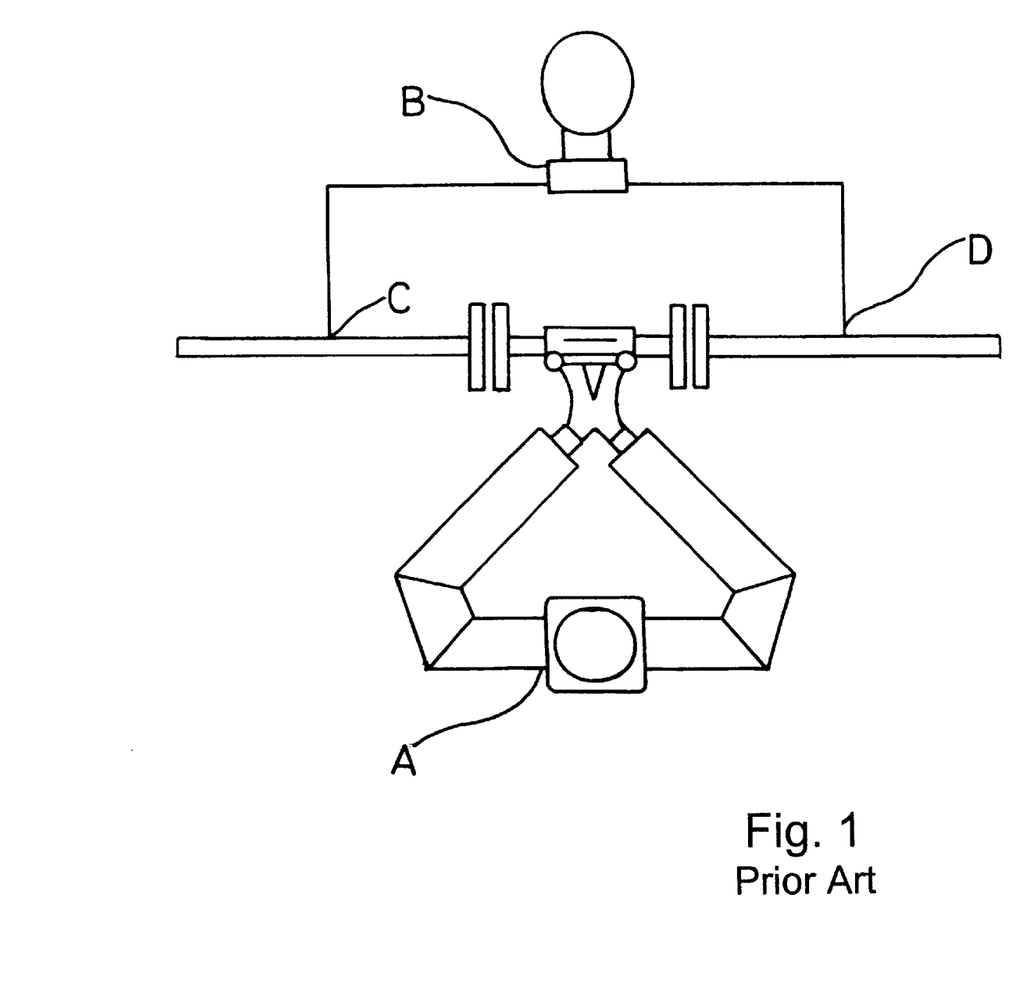
FIG. 1 is a schematic illustration of a prior art viscometer configuration.

Turning to FIG. 1 of the drawings, a prior art on-line viscometer is shown. Specifically, a Coriolis mass flow meter A, equipped with a differential pressure transducer B, is placed directly in the process flow path. Volumetric fluid flow rates are determined by dividing the fluid mass flow rate by the fluid density. The differential pressure transducer measures the pressure drop between a point upstream C of the meter and a point downstream D of the meter. The distance ΔL between points C and D is a known constant. Because of the looped configuration of a Coriolis meter, however, flow disturbances and entrance and exit effects occur in the pressure measurement section. These disturbances and effects lead to fluid flow in the measurement section that is not fully developed and uni-directional, resulting in inaccurate application of the Hagen-Poiseuille equation and Equation A.

In accordance with the present invention, an apparatus is provided having an improved flow path configuration. Because this improved flow path configuration prevents any flow entrance or exit effects and allows for fully developed, undisturbed, and uni-directional flow to occur, the assumptions underlying the Hagen-Poiseuille equation and Equation A are satisfied and improved accuracy in fluid viscosity determination is achieved.

Figure 2:
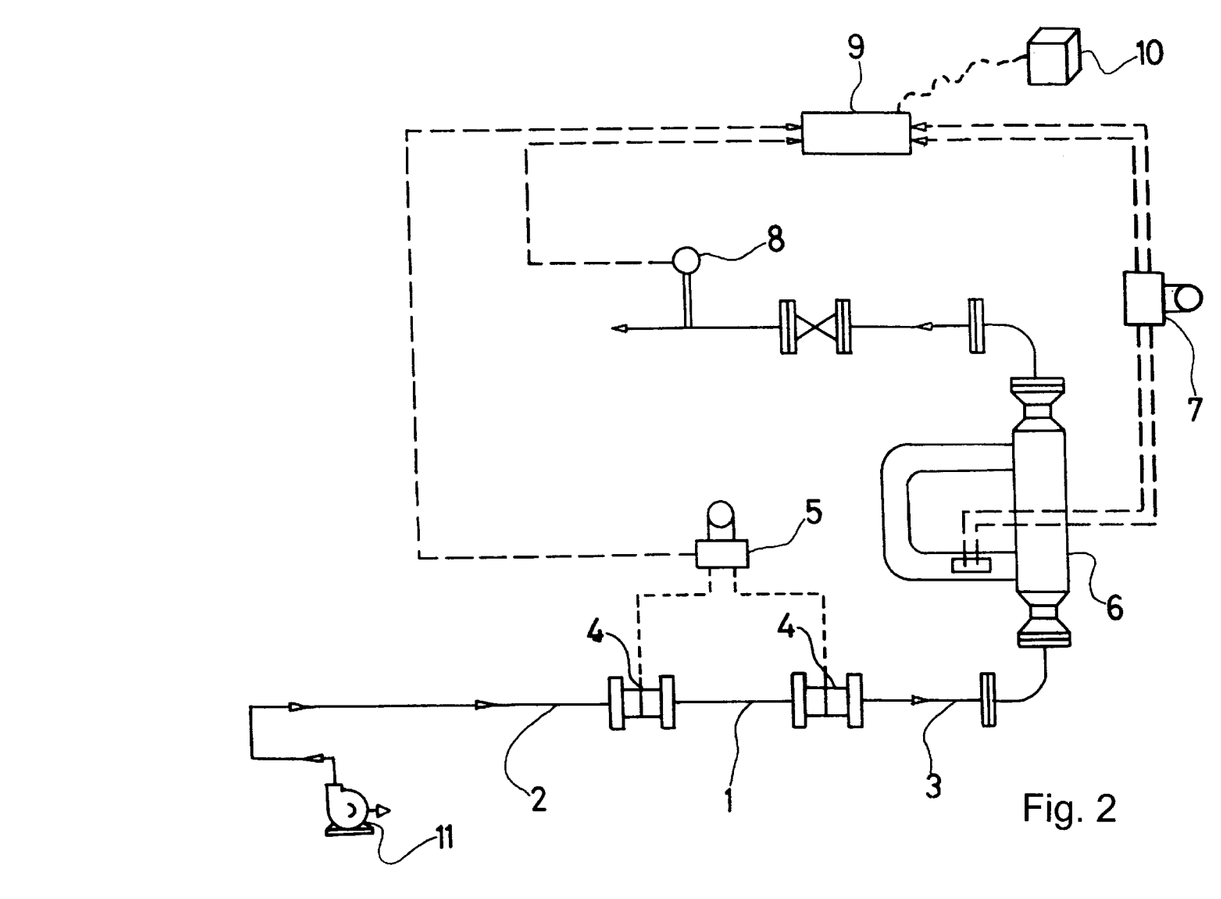
FIG. 2 is a schematic illustration of the preferred embodiment of the apparatus of the invention.

A preferred embodiment of the apparatus of the invention is schematically illustrated in FIG. 2. A substantially straight differential pressure measurement section with substantially uniform inside diameter is provided. The pressure measurement section comprises a differential pressure measurement flow tube 1, a preceding flow tube 2 upstream of the measurement flow tube, and a succeeding flow tube 3 downstream of the measurement flow tube. The inside diameters of both the preceding and succeeding flow tubes are substantially equal to that of the measurement flow tube. The measurement section may be one continuous tube or multiple tube sections connected with non-invasive means, so as to prevent flow disturbances from occurring at the inlet or exit of the measurement flow tube. In the preferred embodiment of the invention, the measurement section is substantially straight and level. It is noted that the measurement section is not required to be level; should it not be level, however, measured differential pressures through the section must be corrected.

A differential pressure measurement device 5 is used to measure the pressure difference of the fluid between the inlet and the outlet of the measurement section. Any means may be used for measuring differential pressure in a substantially non-intrusive manner so that flow remains undisturbed. In the preferred embodiment of the invention, a Rosemount 3051C differential pressure transducer is used. The two pressure taps for the differential pressure transducer are preferably made with WIKA Type 981.10 seals 4, with one located at the inlet of the measurement flow tube, and one at the outlet of the measurement flow tube.

The length of the pressure measurement flow tube 1 should be long enough that differential pressure measurements of a useful magnitude between its inlet and outlet occur. In one embodiment of the invention a measurement flow tube length of about 36 inches is sued with the preferred Rosemount differential pressure transmitter and fluid flow rates between 5 and 60 gpm.

The length of the preceding flow tube 2 should be such that fully developed, undisturbed and uni-directional flow occurs at the inlet of the measurement flow tube. The minimum length of this preceding flow tube can be calculated by the equation:

$$L_m = 0.035 D \times Re$$

where D is the inside tube diameter and Re is the flow Reynolds number. Using this formula with generally expected Reynolds numbers of up to 1200, the preceding flow tube should be at least 40 diameters in length. In the aforesaid embodiment of the invention, the measurement flow tube diameter is 1.61 inches and the preceding tube length is 72 inches.

The length of the succeeding flow tube 3 should be sufficient to avoid exit effects in the pressure measurement flow tube. A length equal to at least 15 times tube inside diameter has been determined to be acceptable. In the embodiment of the invention having an inside diameter of 1.61 inches, a succeeding flow tube length of 40 inches is used.

A non-intrusive means for measuring fluid flow rate is in line with, located either upstream or downstream of the differential pressure measurement section. The flow rate measuring means is located away from the pressure measurement section so as not to cause any flow disturbances within the measurement section. Any means may be used for determining the volumetric flow rate of the fluid. In the preferred embodiment of the invention, the fluid flow rate measuring means 6 comprises a Micro Motion ELITE CMF200 Coriolis mass flow meter with fluid density measuring capabilities located downstream of the succeeding flow tube section, in combination with a Micro Motion ELITE RFT9739 Mass Flow and Density Transmitter 7. Volumetric fluid flow rates are determined by dividing measured fluid mass flow rates by measured fluid densities. It should be understood, however, that although the Coriolis mass flow meter is preferred, the present invention should not be construed as being limited to the Coriolis mass flow meter. There are various and sundry devices known to those skilled in the art for measuring or otherwise determining volumetric flow rate, which may be employed in lieu of the preferred Coriolis mass flow meter.

Fluid is conveyed through the differential pressure measurement section and flow rate measuring means via a pump 11 or other means for providing and/or regulating fluid flow. Substantially steady and non-fluctuating flow is desired. The preferred embodiment of the invention uses a Moyno positive displacement pump for this purpose. It should be understood that one or more devices other than a pump could be employed to regulate fluid flow, such as a valve or throttle.

In the preferred embodiment of the invention, the temperature of the fluid near the differential pressure measurement section and flow rate measuring section is measured using an instrument 8. Temperature data are not used directly to calculate viscosity, but as viscosity can vary greatly with temperature, temperature data are useful. Also, temperature measurements may be useful for compensating differential pressure, flow rate, and density measurements. In the preferred embodiment of the invention, the temperature measurement instrument comprises a resistance temperature detector probe placed downstream of the flow rate measuring means.

In the preferred embodiment of the invention, the differential pressure measuring means, flow rate measuring means, and temperature measuring means each have an output signal conveying measured values. The preferred embodiment further comprises conversion means 9 to convert the output signals form analog to digital, and a microcomputer 10 to receive, convert, calculate, dynamically display and record values including the fluid viscosity, mass flow rate, density, differential pressure, temperature, Reynolds number and velocity.

In the preferred embodiment of the invention, the microcomputer is also programmed to determine the viscosity verses shear rate relationship for non-Newtonian fluids using the power law model previously discussed:

$$\mu = k\dot{\gamma}^{n-1}$$

This is accomplished by first plotting measured differential pressures verse measured flow rates (shear rates) on a log-log format. The slope of the approximately linear plot is equal to the power law index n, and the y axis intercept "C" is equal to a constant from which the power law consistency k may be derived. The microcomputer utilizes a traditional least squares fit method to calculate the plot slope n and y-axis intercept C. Once C is determined, power law consistency k may be derived via:

$$k = e^{ln\ 10} \times (C - n\ \log T - \log(2\Delta L/R))$$

where $$T = (3n+1)/(\pi n R^3)$$

the foregoing equation for k may be reduced to:

$$k = 10^c \left(\frac{D}{4\Delta L}\right)\left(\frac{\pi D^3}{8}\right)^n \left(\frac{n}{3n+1}\right)^n$$

Figure 3:
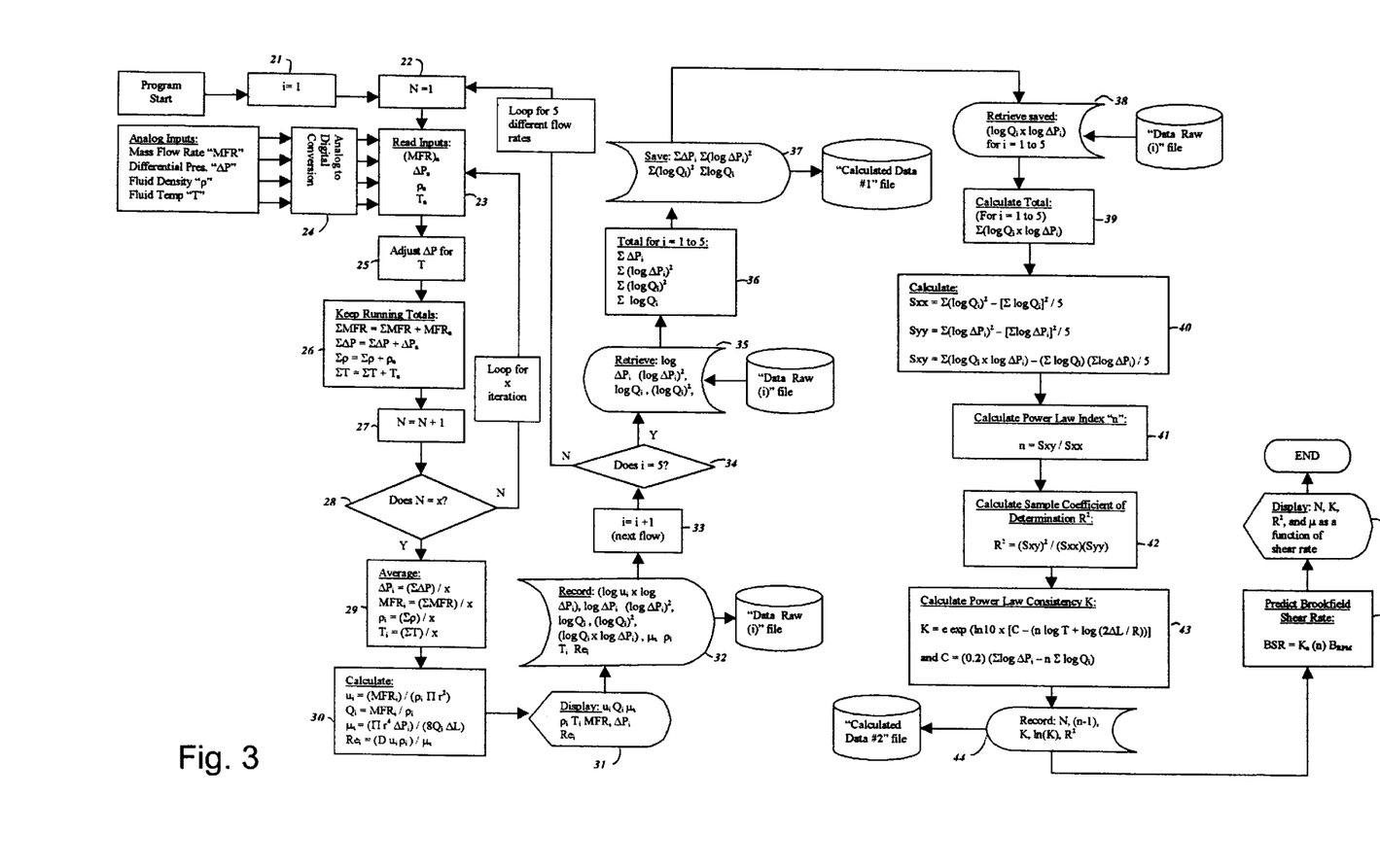
FIG. 3 is a flow chart showing a preferred embodiment of the software for performing the method of the invention.

FIG. 3 is a flow chart showing a preferred embodiment of the software performing a method of the invention. The program begins and first sets a flow iteration counter i equal to 1 (21). This flow iteration variable will be changed for each successive flow rate of the several to be run for power law constant determination purposes. The program then enters an input signal sampling loop and sets a second iteration counter N equal to 1 (22) to keep track of the number of times through the input signal sampling loop. This loop will read input signals over its multitude of iterations to smooth out any fluctuations in a given flow rate.

After being converted from analog to digital by conversion means 24, input signals for measured fluid differential pressure Δp through the pressure measurement section, measured fluid temperature T, measured fluid mass flow rate MFR, and measured fluid density ρ are read by the program 23.

The program then adjusts Δp for temperature T 25. Running sum totals of Δp, T, MFR, and ρ are kept 26, and the loop iteration counter N is increased by 1 (27) to indicate that a set of input signals has been read and added to the running sum totals. Depending on the number of times the loop has already been executed, the program then makes a determination of whether or not to repeat this process of reading and summing input signals 28.

Once the loop has been run for a desired number of iterations, the summed totals of Δp, T, ρ, and MFR are each divided by the number of iterations to calculate average values 29. Using these averaged values, a Reynolds number Re, volumetric flow rate Q, apparent viscosity μ, and fluid velocity v for the current flow rate are calculated 30 using the formulae:

$$Q = MFR/\rho$$

$$\mu = (\pi \Delta p R^4)/(8 \Delta L Q)$$

$$v = (MFR)/(\rho \pi R^2)$$

$$Re = D v \rho / \mu$$

where R is the measurement section tube inside radius, and ΔL is the distance over which the differential pressure is measured. These calculated values, along with T, Δp, MFR and ρ are then displayed 31.

A data file data raw (i) corresponding to the current flow rate is then created and stored 31 with values of log Q, (log Q)², log Δp, (log Δp)², (log v×log Δp), (log ΔQ×log Δp), ρ, T and Re. The flow iteration counter "i" is increased 33 to indicate that a different flow will next be measured, and the program loops back to 22 to repeat measurements at another flow rate.

After the desired number of different flow rates have been run, the program will begin the process of determining the power law viscosity equation constants for the non-Newtonian fluid being investigated. The well known least squares fit model will be utilized to determine a best fit linear slope and y axis intercept for the pressure differential verse flow rate data. The program will first retrieve the stored log Q, (log Q)², log Δp, and (log Δp)² for each of the different flow rates stored in the respective raw data (i) files 35. Each of these 4 retrieved values is then summed over the several flow rates 36, with these summed totals stored to a newly created "calculated data" file 37.

The respective raw data (i) files are again recalled to extract the individual log Q×log Δp values for each flow rate 38. A summed total of these values is then calculated 39. Three variables are then defined and calculated 40:

$$S_{xx} = \Sigma(\log Q)^2 - ((\Sigma \log Q)^2/i)$$

$$S_{yy} = \Sigma(\log \Delta p)^2 - ((\Sigma \log \Delta p)^2/i)$$

$$S_{xy} = \Sigma(\log Q \times \log \Delta p) - ((\Sigma \log Q \times \log \Delta p)/i)$$

where i is the number of flow rates investigated. The power law constant n in the power law equation:

$$\mu = k\dot{\gamma}^{n-1}$$

is then solved 41.

$n = (S_{xy}/S_{xx})$

A sample coefficient of determination $R^2$ is then defined and calculated 42.

$R^2 = (S_{xy})^2/((S_{xx})(S_{yy}))$

The second power law constant k is then solved 43.

$k = e^{ln\ 10} \times (C - n\ \log T - \log(2\Delta L/R))$ where $\Delta L$ is measurement section length, R is measurement section inside radius, and:

$C = (\Sigma \log \Delta p - n\Sigma \log Q)/i$ where i is the number of flow rates investigated. Calculated values of n, (n−1), k, ln, k, and $R^2$ are then saved to a newly created "Calculated data #2" file 44.

Once the power law constants n and k have been determined, a shear rate dependent viscosity can be calculated using the equation:

$\mu_{sr} = k\dot{y}^{n-1}$ where $\mu_{sr}$ is the shear rate dependent viscosity.

In this preferred embodiment of the invention, the computer program then extrapolates the corresponding Brookfield shear rate 45, which is a commonly referenced value in the paper making and coatings industry. This value is predicted by solving the equation:

$BSR = k_n(n)B_{rpm}$ where BSR is the Brookfield shear rate, n is the calculated power law constant, $B_{rpm}$ is the desired revolutions per minute of the Brookfield spindle, and $k_n$ is a Brookfield conversion ratio whose values are stored in a table tabulating n with Brookfield spindle numbers.

The calculated values of n, k, $R^2$, and $\mu_{sr}$ as a function of shear rate are then displayed 46.

The objects and advantages of the invention have thus been shown to be attained in a convenient, economical and facile manner. While the preferred embodiment of the apparatus and method of the invention have been shown and described, it is to be understood that various modifications and changes may be made thereto without departing from the scope of the invention as defined by the appended claims.

What is claimed is:

1. A method of measuring the fluid viscosity of a non-Newtonian fluid, comprising the steps of:
   (a) providing a pipe line, the pipe line including a substantially straight pressure measurement flow tube having a substantially uniform inside diameter;
   (b) developing substantially steady, fully developed, unidirectional, laminar flow upstream of said pressure measurement flow tube;
   (c) conveying the fluid through the pressure measurement flow tube at a first selected flow rate;
   (d) minimizing end effects as the fluid exits the pressure measurement flow tube;
   (e) measuring differential pressure of the fluid between the respective ends of said pressure measurement flow tube;
   (f) measuring the flow rate of the fluid in said pipe line, either upstream or downstream of said pressure measurement flow tube;
   (g) repeating steps (b) through (f) with at least a second flow rate;
   (h) determining power law constants n and k from the flow rate and differential pressure data obtained in steps (b) through (g) at plural flow rates; and
   (i) calculating viscosity $\mu$ with the power law constants determined in step (h).

2. A method of measuring fluid viscosity as in claim 1, further comprising the step of leveling the measurement flow tube before measuring differential pressure.

3. A method of measuring non-Newtonian fluid viscosity as in claim 1, wherein the step of measuring differential pressure between the respective ends of said pressure measurement flow tube is performed with a differential pressure transducer, said differential pressure transducer measuring the differential pressure between a pair of non-intrusive pressure taps on said measurement flow tube at locations separated from the ends of the measurement flow tube such that end effects are avoided.

4. A method of measuring fluid viscosity as in claim 1, wherein the step of measuring the flow rate of the fluid through said pipe line is performed by measuring the mass flow rate of said fluid and the density of said fluid and calculating volumetric flow rate therefrom.

5. A method of measuring fluid viscosity as in claim 1, further comprising the step of measuring the fluid temperature.

6. A method of measuring non-Newtonian fluid viscosity as in claim 1, further comprising the steps of providing a microcomputer, inputting the differential pressure and flow rates into the computer, and programming the computer to calculate fluid viscosity.

7. A method of measuring the fluid viscosity of a non-Newtonian fluid as in claim 1, wherein said viscosity $\mu$ is determined from shear rate y by:

$\mu = k\dot{y}^{n-1}$ by determining the slope n and the y-intercept C of the measured differential pressure versus flow rate on a log-log plot, said power law constant k derived from said y axis intercept C by:

$$k = 10^C \left(\frac{D}{4\Delta L}\right)\left(\frac{\pi D^3}{8}\right)^n \left(\frac{n}{3n+1}\right)^n$$

where $\Delta L$ is the length of the pressure measurement flow tube.

8. A method of measuring the fluid viscosity of a non-Newtonian fluid as in claim 1, wherein the step of determining power law constants n and k, comprises determining n from a log-log plot of $\Delta P$ versus Q, and calculating k using the n value determined from the log-log plot.

9. A method of measuring the fluid viscosity of a non-Newtonian fluid, comprising the steps of:
   (a) providing a pipe line, the pipe line including a straight, level pressure measurement flow tube with substantially uniform inside diameter D;
   (b) developing substantially steady, fully developed, unidirectional laminar flow at a selected flow rate upstream of the pressure measurement flow tube;
   (c) conveying the fluid through the pressure measurement flow tube at the selected flow rate;
   (d) minimizing end effects as the fluid exits the pressure measurement flow tube;
   (e) measuring differential pressure $\Delta P$ of the fluid between the respective ends of the flow tube;

(f) measuring the mass flow rate MFR of the fluid in the pipe line, either upstream or downstream of the pressure measurement flow tube;

(g) measuring the density ρ of the fluid in the pipe line;

(h) repeating steps (b) through (g) for several different flow rates; and (i) inputting said mass flow rate, density, and differential pressure measurements to a microcomputer, said microcomputer programmed to determine viscosity $\mu$ from shear rate y by the equation:

$$\mu = ky^{n-1}$$

where power law constants k and n are determined by plotting $\Delta P$ verses Q on a log-log plot, where volumetric flow rate Q is:

$$Q = \frac{MFR}{\rho}$$

with n equal to the slope of said plot, and said power law constant k derived from the y axis intercept C of said plot by:

$$k = 10^c \left(\frac{D}{4\Delta L}\right)\left(\frac{\pi D^3}{8}\right)^n \left(\frac{n}{3n+1}\right)^n$$

where $\Delta L$ is the length of the pressure measurement flow tube.

10. A method of measuring the fluid viscosity of a non-Newtonian fluid, comprising the steps of:

(a) providing a pipe line, the pipe line including a straight pressure measurement flow tube with substantially uniform inside diameter D;

(b) developing substantially steady, fully developed, unidirectional laminar flow at a selected flow rate upstream of the pressure measurement flow tube;

(c) conveying the fluid through the pressure measurement flow tube at the selected flow rate;

(d) measuring differential pressure $\Delta P$ of the fluid between the respective ends of the flow tube;

(e) measuring the flow rate of the fluid in the pipe line;

(f) repeating steps (b) through (e) for a different flow rate; and (g) calculating viscosity $\mu$ from shear rate y by the equation:

$$\mu = ky^{n-1}$$

where power law constants k and n are determined by plotting $\Delta P$ verses Q on a log-log plot, with n equal to the slope of said plot, and said power law constant k calculated by:

$$k = 10^c \left(\frac{D}{4\Delta L}\right)\left(\frac{\pi D^3}{8}\right)^n \left(\frac{n}{3n+1}\right)^n$$

where C is the y-axis intercept of said plot, D is the inside pipe diameter, and $\Delta L$ is the length of the pressure measurement flow tube.

* * * * *

UNITED STATES PATENT AND TRADEMARK OFFICE
CERTIFICATE OF CORRECTION

PATENT NO.    : 6,196,058 B1                                Page 1 of 1
DATED         : March 6, 2001
INVENTOR(S)   : Chen It is certified that error appears in the above-identified patent and that said Letters Patent is hereby corrected as shown below:

Title page,
Item [56] References Cited:

Delete "3,838,598     10/1974 Tompkins"
Delete "5,172,585     12/1992 Gleissle"
Insert -- 4,425,790    1/1984 Bice et al. --
Insert -- 4,642,132    11/1986 Parnaby et al --
Insert -- 5,257,529    11/1993 Taniguchi et al --
Insert -- 5,708,1998   1/1998 Todd et al --
Insert -- Covas et al, Rheological Fundamentals of Polymer Processing, 1995, pp. 145-147, Kluwer Academic Publishers --

Column 6,
Line 19, delete "sued" and insert -- used --

Column 7,
Line 25, delete "form" and insert -- from --

Signed and Sealed this

Fourteenth Day of May, 2002

Attest:

JAMES E. ROGAN
*Attesting Officer*         *Director of the United States Patent and Trademark Office*

UNITED STATES PATENT AND TRADEMARK OFFICE
CERTIFICATE OF CORRECTION

PATENT NO. : 6,196,058 B1
DATED : March 6, 2001
INVENTOR(S) : Chen

It is certified that error appears in the above-identified patent and that said Letters Patent is hereby corrected as shown below:

Column 1,
Line 39, delete "$\mu = k\dot{y}^{n-1}$" and insert -- "$\mu = k\dot{\gamma}^{n-1}$" --

Line 40, delete "$\dot{y}$" and insert -- "$\dot{\gamma}$" --

Column 7,
Line 35, delete "$\mu = k\dot{y}^{n-1}$" and insert -- "$\mu = k\dot{\gamma}^{n-1}$" --

Column 8,
Line 65, delete "$\mu = k\dot{y}^{n-1}$" and insert -- "$\mu = k\dot{\gamma}^{n-1}$" --

Column 9,
Line 22, delete "$\mu = k\dot{y}^{n-1}$" and insert -- "$\mu = k\dot{\gamma}^{n-1}$" --

Column 10,
Line 35, delete "$\dot{y}$" and insert -- "$\dot{\gamma}$" --
Line 37, delete "$\mu = ky^{n-1}$" and insert -- "$\mu = k\dot{\gamma}^{n-1}$" --

Column 11,
Line 10, delete "$\dot{y}$" and insert -- "$\dot{\gamma}$" --
Line 12, delete "$\mu = ky^{n-1}$" and insert -- "$\mu = k\dot{\gamma}^{n-1}$" --

Column 12,
Line 14, delete "$\dot{y}$" and insert -- "$\dot{\gamma}$" --
Line 17, delete "$\mu = ky^{n-1}$" and insert -- "$\mu = k\dot{\gamma}^{n-1}$" --

Signed and Sealed this

Eighth Day of April, 2003

JAMES E. ROGAN
*Director of the United States Patent and Trademark Office*